US00PP24317P3

(12) United States Plant Patent
Ferguson et al.

(10) Patent No.: US PP24,317 P3
(45) Date of Patent: Mar. 18, 2014

(54) STRAWBERRY PLANT NAMED 'DRISSTRAWTHIRTYONE'

(50) Latin Name: *Fragaria×ananassa*
Varietal Denomination: DrisStrawThirtyOne

(75) Inventors: Michael D. Ferguson, Moorpark, CA (US); Terrance C. Moran, Ojai, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 54 days.

(21) Appl. No.: 13/507,373

(22) Filed: Jun. 22, 2012

(65) Prior Publication Data

US 2013/0347158 P1 Dec. 26, 2013

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — Jondle Plant Sciences Division of Swanson & Bratschun, L.L.C.

(57) ABSTRACT

A new and distinct variety of strawberry plant named 'DrisStrawThirtyOne' particularly characterized by large fruit with sweet juicy flavor, conic shape and full red glossy color is disclosed.

3 Drawing Sheets

Genus and species: *Fragaria×ananassa.*
Variety denomination: 'DrisStrawThirtyOne'.

BACKGROUND OF THE NEW PLANT

The present invention relates to a new and distinct strawberry variety designated 'DrisStrawThirtyOne' and botanically known as *Fragaria×ananassa*. This new strawberry variety was discovered in Ventura County, Calif. in October 2007 and originated from a cross between the proprietary female parent 'DrisStrawThree' (U.S. Plant Pat. No. 19,673) and the proprietary male parent '508M172' (unpatented). A single plant was selected for asexual propagation via tissue culture and vegetative cuttings in Shasta County, Calif. in 2007.

'DrisStrawThirtyOne' underwent further testing in Ventura County, Calif. for five years (2008-2012). The present invention has been found to retain its distinctive characteristics through successive asexual propagations via stolons and tissue culture.

Plant Breeder's Rights for this variety have not been applied for. 'DrisStrawThirtyOne' has not been made publicly available or sold more than one year prior to the filing date of this application.

SUMMARY OF THE INVENTION

The following are the most outstanding and distinguishing characteristics of this new cultivar when grown under normal horticultural practices in Ventura County, Calif.

1. Large fruit with sweet juicy flavor;
2. Conic shape; and
3. Full red glossy color.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from four-month-old plants.

DESCRIPTION OF THE NEW VARIETY

Figure 1:
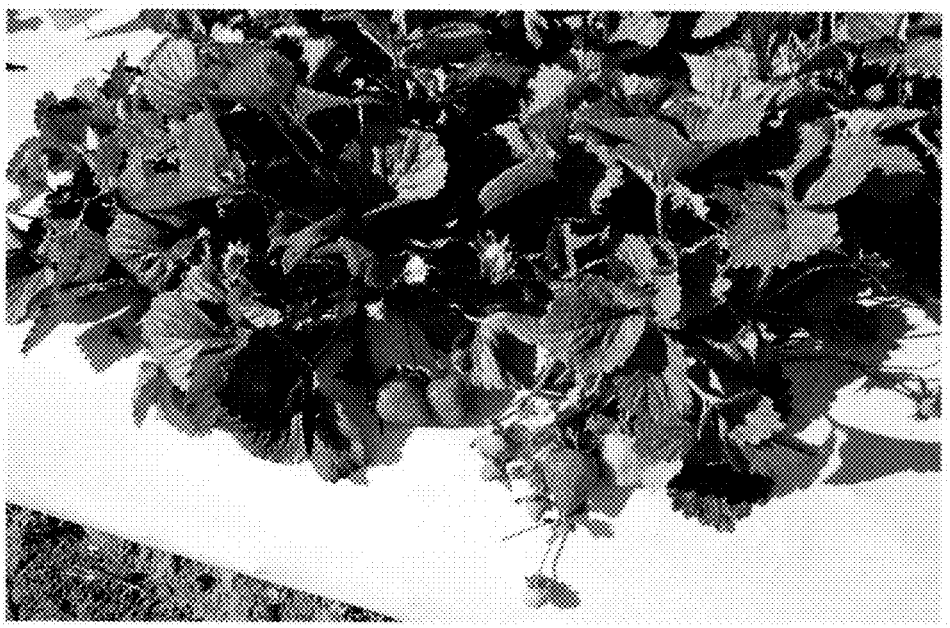
FIG. 1 shows overall plant habit including fruit at various stages of development.
Figure 2:
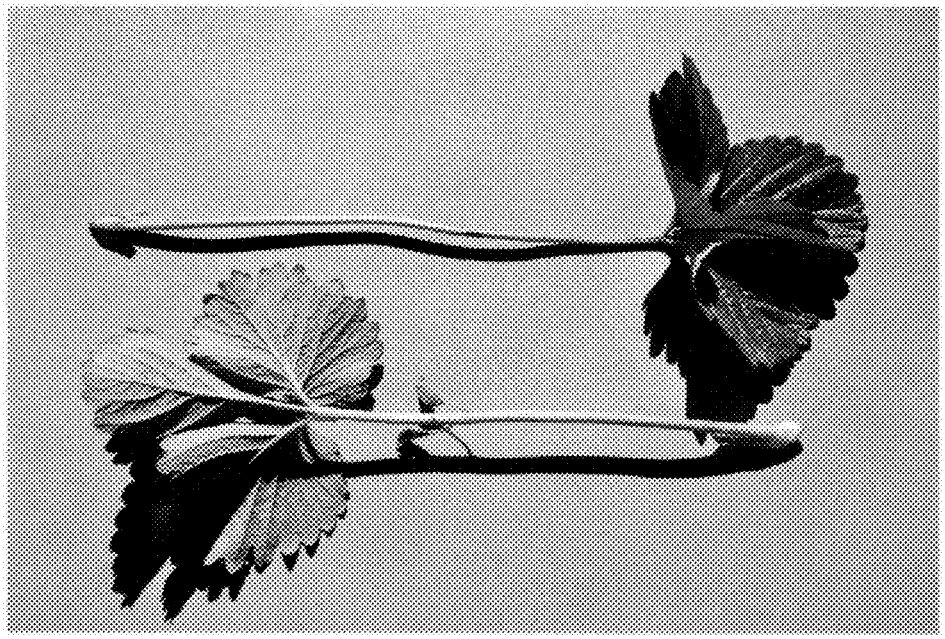
FIG. 2 shows upper and lower surfaces of the leaves of the plant with three leaflets.
Figure 3:
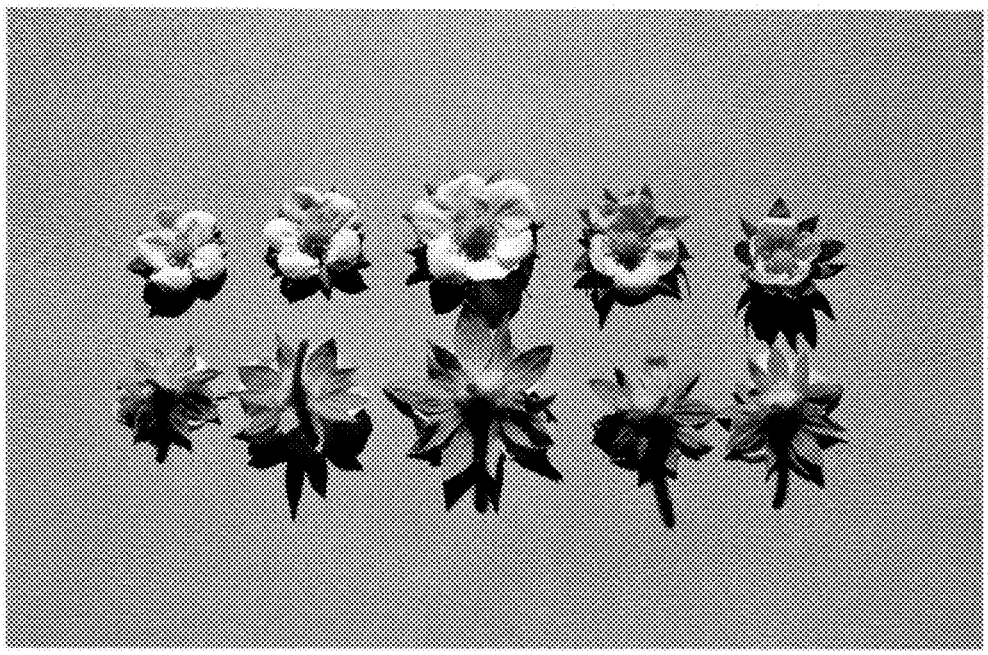
FIG. 3 shows both upper and lower surfaces of the flowers.
Figure 4:
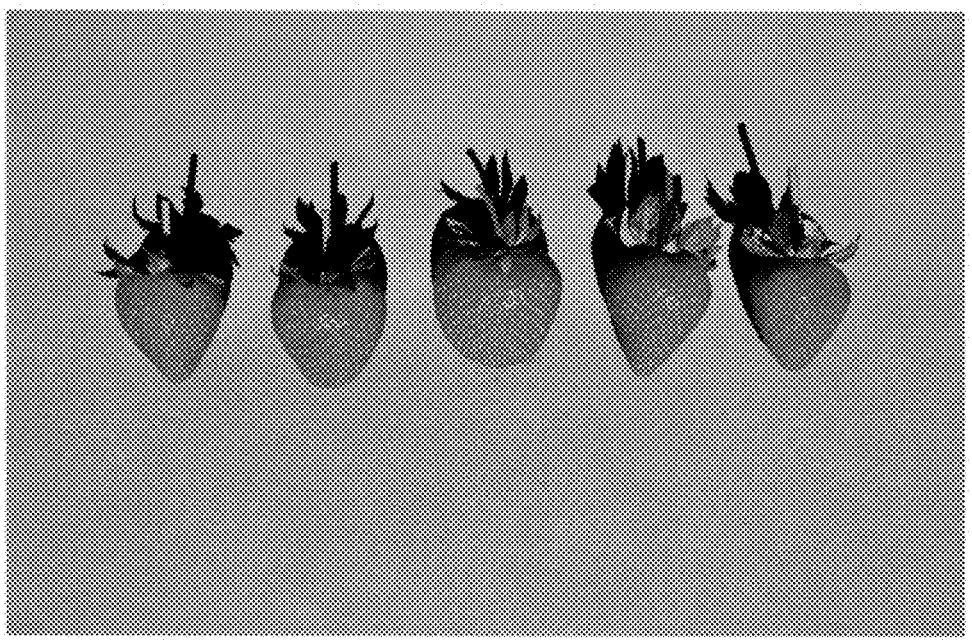
FIG. 4 shows the whole fruit.
Figure 5:
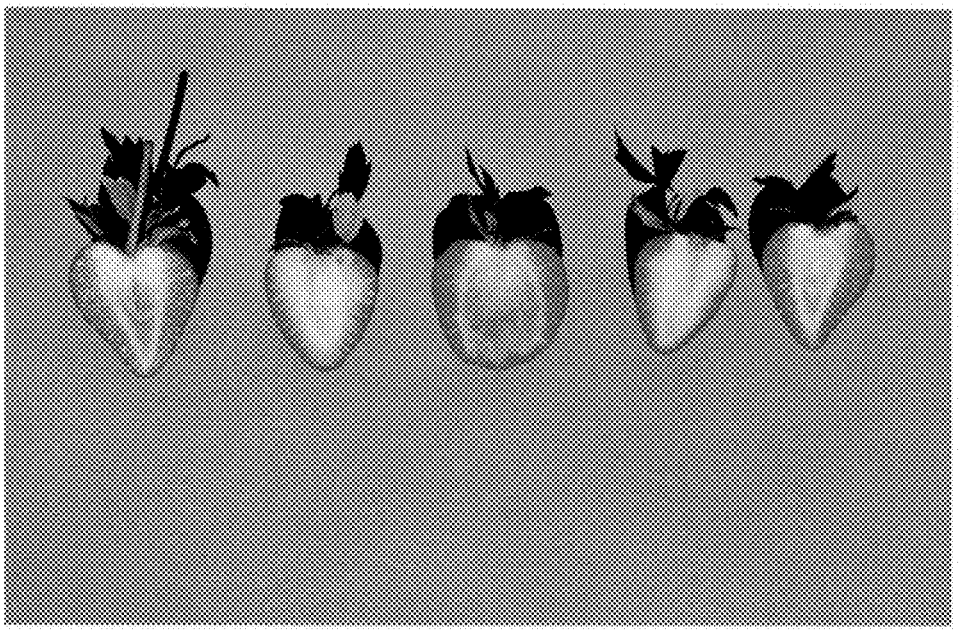
FIG. 5 shows the fruit in longitudinal cross-section.

The following detailed descriptions set forth the distinctive characteristics of 'DrisStrawThirtyOne'. The data which define these characteristics is based on observations taken in Ventura County, Calif. from 2008 to 2012. This description is in accordance with UPOV terminology. Color designations, color descriptions, and other phenotypical descriptions may deviate from the stated values and descriptions depending upon variation in environmental, seasonal, climatic, and cultural conditions. 'DrisStrawThirtyOne' has not been observed under all possible environmental conditions. The botanical description of 'DrisStrawThirtyOne' was taken from four-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawThirtyOne'.

Parentage:

*Female parent.*—The proprietary variety 'DrisStraw-Three' (U.S. Plant Pat. No. 19,673).

*Male parent.*—The proprietary variety '508M172' (unpatented).

Plant:

*Height.*—28.7 cm.

*Diameter.*—48.3 cm.

*Number of crowns/plant.*—3.

*Habit.*—Upright.

*Density of individual plant.*—Medium.

*Vigor* (*health and hardiness of plant*).—Strong.

Terminal leaflets:

*Size.*—Medium. Length: 8.0 cm. Width: 7.2 cm. Length/width ratio: 1.1.

*Number of teeth/terminal leaflet.*—21.

*Shape of teeth.*—Obtuse — serrate to crenate.

*Color.*—Upper surface: RHS N137A (Dark green). Lower surface: RHS 148C (Medium yellow-green).

*Shape in cross section.*—Concave.

*Blistering.*—Weak.

*Glossiness.*—Medium.

*Number of leaflets.*—Three only.

*Shape.*—Orbicular.

*Base shape.*—Rounded.

*Apex descriptor.*—Rounded.

*Variegation.*—Absent.

*Margin.*—Crenate.

*Margin profile.*—Flat.

Petiole:

*Length.*—Long; 18.5 cm.

*Diameter.*—3.36 mm.

*Pubescence.*—Absent or very sparse.

*Pose of hairs.*—Outwards — horizontal.

*Color.*—RHS 144B (Medium yellow-green).

Petiolule:

*Length.*—9.06 mm.

*Diameter.*—1.51 mm.

*Bract frequency.*—0.

*Pubescence.*—Absent or very sparse.

*Pose of hairs.*—Outwards — horizontal.

*Color.*—RHS 144A (Medium yellow-green).

Stipule:

*Length.*—2.9 cm.

*Width.*—7.82 mm.

*Pubescence.*—Dense.

*Stipule anthocyanin coloration.*—Weak; RHS 68B (Medium red-purple).

Stolon:

*Number.*—Medium.

*Average number of daughter plants per plant.*—13.

*Stolon anthocyanin.*—Very strong; RHS 47B (Red).

*Diameter at bract.*—3.30 mm.

*Thickness.*—Very thick.

*Pubescence.*—Dense.

Inflorescence:

*Position relative to foliage.*—Beneath.

*Number of flowers.*—Medium.

*Time of flowering* (*50% of plants at first flower*).—Early.

*Flower size.*—Medium.

*Diameter.*—27.38 mm.

*Petals.*—Shape: Orbicular. Apex: Rounded. Base: Concave — convex. Margin: Entire. Spacing: Overlapping. Length: 14.04 mm. Width: 14.32 mm. Length/width ratio: 1.0 (As long as broad). Petal number per flower: 5. Color (upper surface): RHS NN155A (White).

*Calyx.*—Diameter: 32.92 mm. Diameter relative to corolla: Larger. Inner calyx diameter relative to outer: Same size. Insertion of calyx: Level. Pose of calyx segments: Reflexed — upwards. Size of calyx in relation to fruit: Slightly larger. Adherence of calyx: Strong.

*Sepal.*—Shape: Elliptical. Apex: Convex. Margin: Entire. Length: 13.21 mm. Width: 5.81 mm. Sepal number per flower: 10.

*Receptacle color.*—RHS 151B (Medium yellow-green).

*Stamen.*—Present. Anther color: RHS 163B (Medium greyed-orange).

*Pedicel.*—Attitude of hairs: Upwards.

Fruiting truss:

*Length.*—21.8 cm.

*Diameter at base of truss.*—4.66 mm.

*Number of berries per fruiting truss.*—5.

*Attitude at first picking.*—Prostrate.

*Pubescence.*—Dense.

*Pose of hairs.*—Outwards — horizontal.

*Color at base of truss.*—RHS 144B (Medium yellow-green).

Fruit:

*Relative fruit size.*—Large.

*Length.*—47.21 mm.

*Width.*—43.27 mm.

*Length/width ratio.*—1.1.

*Fruit hollow length.*—16.16 mm.

*Fruit hollow width.*—9.88 mm.

*Fruit hollow length/width ratio.*—1.6 (Longer than broad).

*Fruit hollow center* (*cavity*).—Small.

*Weight* (*per individual berry*).—30.8 g.

*Predominant fruit shape.*—Conical.

*Difference in shape between primary and secondary fruits.*—Slight.

*Evenness of fruit surface.*—Even or very slightly uneven.

*Fruit skin color.*—RHS 46A (Dark red).

*Evenness of fruit color.*—Even or very slightly uneven.

*Fruit glossiness.*—Medium.

*Achenes.*—Insertion of achenes: Level with surface. Coloration (sunward side of berry): RHS 20B (Medium yellow-green). Coloration (shaded side of berry): RHS 153B (Medium yellow-green). Number per berry: 132. Weight (weight of achenes divided by total # seed): 0.000968365 g. Width of band without achenes: Narrow.

*Firmness of flesh* (*when fully ripe*).—Firm.

*Color of flesh* (*excluding core*).—RHS 34A (Medium red).

*Color of core.*—RHS 155B (White).

*Evenness of flesh color.*—Slightly uneven.

*Distribution of flesh color.*—Only marginal.

*Sweetness.*—Medium.

*Acidity.*—Weak.

*Texture when tasted.*—Fine.

*Type of bearing.*—Fully everbearing — fully remontant.

*Grams of fruit/plant.*—524.0 g.

*Harvest interval.*—August-mid-January.

*Harvest maturity.*—Early.

Disease, pest, and stress resistance:

*Tetranychus urticae.*—Moderately susceptible.
*Tarsonemus pallidus.*—Moderately susceptible.
*Aphelenchoides fragariae.*—Moderately susceptible.
*Pratylenchus penetrans.*—Moderately susceptible.
*Ditylenchus dipsaci.*—Moderately susceptible.
*Anthonomus rubi.*—Moderately susceptible.
*Aphis spp.* (*Aphids*).—Moderately susceptible.
*Lygus hesperus* (*Lygus bug*).—Moderately susceptible.
*Botrytis fruit rot.*—Moderately susceptible.
*Powdery mildew.*—Moderately resistant.
*Verticillium wilt.*—Moderately susceptible.
*Leather rot.*—Moderately susceptible.
*Ramularia tulasnei* (*Leaf spots*).—Moderately susceptible.
*Black root rot.*—Moderately susceptible.
*Strawberry mottle virus.*—Moderately susceptible.
*Xanthomonas fragariae.*—Moderately susceptible.
*High pH.*—Moderately resistant.
*High soil salt levels.*—Moderately resistant.

COMPARISON WITH PARENTAL AND COMMERCIAL VARIETIES

When 'DrisStrawThirtyOne' is compared to the proprietary female parent 'DrisStrawThree' (U.S. Plant Pat. No. 19,673), 'DrisStrawThirtyOne' has an upright habit with medium density, medium glossy leaves, and conical shaped fruit, whereas 'DrisStrawThree' has a dense, flat globose habit, weakly glossy leaves, and almost cylindrical shaped fruit. Additionally, 'DrisStrawThirtyOne' has a earlier fruiting and firmer fruit than 'DrisStrawThree'.

When 'DrisStrawThirtyOne' is compared to the proprietary male parent '508M172' (unpatented), 'DrisStrawThirtyOne' has a more compact plant habit, larger and darker fruit, better rain tolerance, and higher yield than '508M172'.

When 'DrisStrawThirtyOne' is compared to the commercial variety 'DrisStrawTwentyOne' (U.S. Plant Pat. No. 23,506), 'DrisStrawThirtyOne' has medium dense plants with weak leaf blistering and medium stolon number, whereas 'DrisStrawTwentyOne' has dense plants with medium leaf blistering and few stolons.

We claim:

1. A new and distinct variety of strawberry plant named 'DrisStrawThirtyOne' as described and shown herein.

* * * * *